United States Patent [19]
Mabille

[11] Patent Number: 4,676,749
[45] Date of Patent: Jun. 30, 1987

[54] NOZZLE HEAD FOR THE HAND PIECE OF A DENTAL PROPHYLACTIC APPARATUS

[75] Inventor: Pierre Mabille, Le Sentier, Switzerland

[73] Assignee: EMS Electro Medical Systems, S.A., Switzerland

[21] Appl. No.: 706,090

[22] Filed: Feb. 27, 1985

[30] Foreign Application Priority Data

Mar. 8, 1984 [DE] Fed. Rep. of Germany ... 8407156[U]
Dec. 21, 1984 [DE] Fed. Rep. of Germany ....... 3447744

[51] Int. Cl.⁴ .............................................. A61C 3/02
[52] U.S. Cl. ........................................ 433/88; 51/439
[58] Field of Search ...................... 433/88, 80, 84, 85; 51/439

[56] References Cited

U.S. PATENT DOCUMENTS

| | | | |
|---|---|---|---|
| 1,779,850 | 10/1930 | Maurer | 433/217.1 |
| 2,532,655 | 12/1950 | Backer | 51/439 |
| 2,587,184 | 2/1952 | Marjama | 51/439 |
| 2,709,852 | 6/1955 | Maurer et al. | 433/88 |
| 2,751,716 | 6/1956 | Pletcher | 51/439 |
| 4,218,855 | 8/1980 | Wemmer | 51/439 |
| 4,412,402 | 11/1983 | Gallant | 433/88 |
| 4,462,803 | 7/1984 | Landgraf et al. | 433/88 |
| 4,492,575 | 1/1985 | Mabille | 51/439 |

FOREIGN PATENT DOCUMENTS 788508 10/1935 France .................................. 433/80

Primary Examiner—John J. Wilson
Attorney, Agent, or Firm—Ratner & Prestia

[57] ABSTRACT

A nozzle head for the hand piece of a dental prophylactic apparatus comprises a connector having two members that are centered with respect to each other along an axis that is in common with the connecting end of an inner tube with a supply line for an abrasive powder material in mixture with air under pressure and also in common with the connecting end of an outer tube as fixed to the same connector member with a supply line for water under pressure through a transverse bore extending between the two connector members, the inner and outer tubes forming first and second orifices that preferably open towards a cup-shaped hollow space formed by a coaxially arranged circular collar.

15 Claims, 2 Drawing Figures

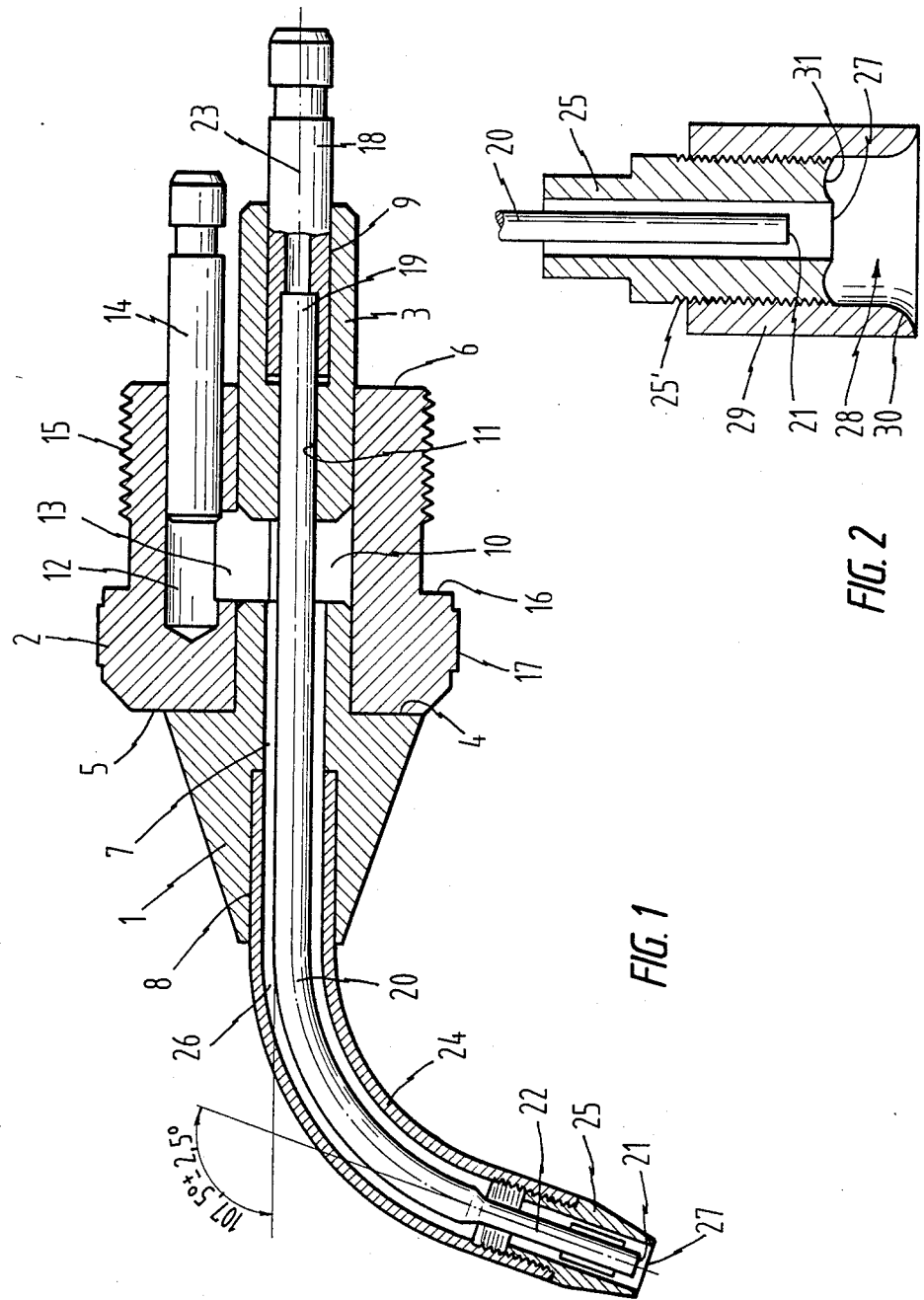

NOZZLE HEAD FOR THE HAND PIECE OF A DENTAL PROPHYLACTIC APPARATUS

FIELD OF THE INVENTION

The present invention is directed to a nozzle head for the hand piece of a prophylactic apparatus for cleaning teeth.

BACKGROUND ART

A prior art nozzle head of the kind as herein referred is described in U.K. Pat. No. 2,026,359. The hand piece comprises a member in the form of a sleeve fixed to a first connector member having two axially parallel bores to which two flexible supply tubes surrounded by said sleeve are connected for supplying the nozzle head with an abrasive powder material in mixture with air under pressure and with water, respectively, as delivered from a dental prophylactic apparatus. The first connector member in turn is connected with a second connector member by means of two slightly angled ridgid tubes of which the one tube in turn is connected with a central bore of this second connector member whereas the other tube in turn is connected with a coaxially arranged second bore in such a manner that the common axis of these two bores into which an inner tube and an outer tube, respectively, are fixedly inserted intersects the axes of the two supply tubes each at a right angle in such mutually apart positions that the supply tube for the abrasive powder material in mixture with air under pressure is connected through said central bore to said inner tube upstream to a circular gap which is provided between said inner tube and said outer tube and which is connected through a transverse bore to the supply tube for water. The inner tube which actually projects over said second connector member ends in a first orifice of the nozzle head as does also the outer tube that accordingly ends in a second orifice at an axially projecting position in respect to said first orifice to thereby obtain an ejection of water from said second orifice that surrounds the central ejection of air under pressure in mixture with the abrasive powder material as provided by said first orifice of the nozzle head for their common application to the surface of a tooth which is to be cleaned by the dentist through any suitable manipulation of the hand piece.

However, the employment of such known nozzle heads still has some considerable disadvantages among which first their relative complex structure resulting in respectively high manufacturing and assembling costs may be stated. Secondly, with such known nozzle heads there generally exists the danger of a clogging of the inner tube of the second connector member mainly at the position where its interconnected bore intersects the supply tube for the abrasive powder material in mixture with the air stream due to the fact that the vacuum zone which is created by the water stream at the orifice of the outer tube causes a suction that draws water droplets in the form of a very fine mist into the inner tube so that the inner wall of the same becomes wet. There further exists with such known nozzle heads in general the system bound disadvantage that with the removal of stains and of plaque and light tartar as therewith practiced a more or less eroded tooth surface with a characteristic dull appearance due to the abrasive action of the abrasive laden air jet may be left so that with the usually followed polishing of the cleaned tooth surface a sometimes considerable loss of the tooth enamel surface could be the rule.

SUMMARY OF THE INVENTION

The present invention is directed to providing a nozzle head for the hand piece of a dental prophylactic apparatus which requires a reduced manufacturing and assembling work by the provision of a more effective feeding of the abrasive powder material in mixture with air under pressure and of water under pressure from the prophylactic apparatus to the two orifices of the nozzle head. A still further and more general object of the present invention is directed to providing a nozzle head which secures for its ejection of air under pressure in mixture with an abrasive powder material and the surrounding ejection of water under pressure a less detrimental eroding effect on the tooth surface to be cleaned sc that the prophylactic procedure as practiced with such a nozzle head becomes less harmful to the enamel surface of the tooth.

These objects are achieved with a nozzle head for the hand piece of a dental prophylactic apparatus which essentially comprises the improvement that two individually manufactured members of a connector are centered with respect to each other with an axis that is in common with a first bore through which a supply line for an abrasive powder material in mixture with air under pressure and extending from the prophylactic apparatus is connected to an inner tube as fixed to the one connector member and ending in a first orifice whereas a second axially parallel bore is provided in the second connector member as adapted for a connection with a supply line for water under pressure extending also from the prophylactic apparatus and being connected through a transverse bore extending between the two connector members to an outer tube as fixed to the one connector member and ending in a second orifice coaxially arranged to the orifice of the inner tube.

According to another main feature of the present invention the two orifices of the nozzle head are arranged within a circular collar that provides a cup-shaped hollow space downstream of the two orifices, the axial length of this hollow space being larger than the inner diameter of the circular collar at the orifice from which water is ejected under pressure.

BRIEF DESCRIPTION OF THE DRAWINGS

FIG. 1 is a longitudinal section of a nozzle head and its connector in accordance with the present invention; and FIG. 2 is an enlarged longitudinal section only of the tip of the nozzle head of FIG. 1 in accordance with a different embodiment of the present invention.

DESCRIPTION OF THE PREFERRED EMBODIMENTS

Referring to FIG. 1, the nozzle head of the present invention comprises a first member 1 and a second member 2 of a connector that is adapted for being screwed into a sleeve member forming the hand piece of a dental prophylactic apparatus as for example described in U.S. Pat. No. 4,492,575. The one connector member 1 has an axially extending centering pin 3 over which the second connector member 2 is fitted so that the two members 1,2 are centered with respect to each other along a common axis with the face 5 of the member 2 in contact with a ring shoulder 4 of the connector member 1. The centering pin 3 has an axial length larger than the axial length of the connector member 2 so that it axially projects over the backside surface 6 of the connector member 2 which by means of any suitable adhesive or by means of a weld is connected fast to the centering pin 3 of the connector member 1.

The connector member 1 is provided with an axial through bore 7 which at its one end has an enlarged counterbore 8, the diameter of the bore 7 being preferably equal to the diameter of a counterbore 9 at the axially projecting end of the centering pin 3. Intermediate these two counterbores 8,9 the connector member 1 is provided with a transverse bore 10 that extends at a right angle to the axial bore 7 which upstream of this transverse bore 10 is provided over a portion of the centering pin 3 with a diameter portion 11 that is smaller than its axially extended counterbore 9. The transverse bore 10 of the connector member 1 as clearly shown in the drawing is airsealed by the surrounding connector member 2.

The connector member 2 is formed as a ring member the inner bore diameter of which of course corresponds to the outer diameter of the centering pin 3 of the connector member 1 and to which a pocket bore 12 extends axially parallel so that this pocket bore 12 is also axially parallel to the bore 7 of the connector member 1 with the transverse bore 10 of which it communicates through a transverse bore 13 extending also at a right angle to the axial bore of the connector member 2. A hollow plug 14 is inserted into the axially parallel bore 12 of the connector member 2 which is provided with an outer thread 15 with which an inner thread of the sleeve member (not shown) of the hand piece corresponds so that this sleeve member accordingly may be screwed onto the connector member 2 for being tightened against a ring shoulder 16 formed by a knurled portion 17 of the connector member 2.

The hollow plug 14 serves as a slip-on means for a first supply line in the form of a flexible tube (not shown) through which water under pressure is supplied from the dental prophylactic apparatus in the manner as described in U.S. Pat. No. 4,492,575. A second flexible tube also connected to such an apparatus and serving as a second supply line for an abrasive powder material in mixture with air under pressure may similarily be slipped on a second hollow plug 18 which is inserted into the counterbore 9 of the centering pin 3 whereby an axially projecting length of this second hollow plug 18 larger than the axially projecting length of the first hollow plug 18 shall prevent an interchanging of the connection of the two flexible tubes which will become arranged within the sleeve member of the hand piece into which the connector member 2 is threaded.

The hollow plug 18 is fitted to the one end 19 of an inner tube 20 that is airtightly inserted into the smaller diameter portion 11 of the centering pin 3 for a mutually centered arrangement along an axis 23 that forms the common centering axis of the two connector members 1,2 and the hollow plug 18. The other end of this inner tube 20 is provided with an orifice 21 of a slightly reduced diameter at the end of a straight portion the axis 22 of which is arranged in respect to the common centering axis 23 of the two connector members 1,2 and the hollow plug 18 at a curved portion of the inner tube 20 of which the radius of curvature corresponds to a central angle of about 107,5° ±2,5° . The inner tube 20 through which accordingly an abrasive powder material in mixture with air under pressure is supplied to its orifice 21 is coaxially arranged over a portion of its length within an outer tube 24 the one end of which is inserted into the counterbore 8 of the connector member 1 and the other end of which is provided with a screw-in orifice member 25 that axially centers the orifice 21 of the inner tube 20 in respect to which the outer tube 24 is arranged with a circular gap 26 inbetween. The orifice member 25 provides for the outer tube 24 a second orifice 27 at a slightly axially projecting position in respect to the orifice 21 of the inner tube 20 so that with the axial gap 26 communicating through the aligned axial bore 7 with the transverse bore 10 of the connector member 1 and through the transverse bore 13 with the pocket bore 12 of the connector member 2 an ejection of water under pressure is obtained with this orifice 27 that surrounds a central ejection of air under pressure in mixture with the abrasive powder material. Since with this arrangement the abrasive laden air stream as supplied through the inner tube 20 accordingly comes into contact with the water stream as supplied through the outer tube 24 only downstream of the orifice 21 there exists no danger for a clogging of this nozzle head the inidividual parts of which are simple to manufacture and also simple to assemble with a final arrangement of the nozzle head on the hand piece of a dental prophylactic apparatus that allows the dentist an improved visibility of the tooth surface from which stains, plaque and/or tartar are to be removed.

For the embodiment shown in FIG. 2 preferably the same assembly principle is realized as for the nozzle head of FIG. 1 for obtaining a central ejection of air under pressure in mixture with an abrasive powder material from a first orifice 21 at the end of an inner tube 20 and a surrounding ejection of water under pressure from a second orifice 27 as provided by a separate orifice member 25 fixed to an outer tube corresponding to the outer tube 24. The orifice member 25 in this case, however, is provided with an outer fine-pitch thread 25′ for allowing a circular collar 29 having a corresponding inner thread to be screwed on the orifice member 25 in an axially adjustable manner with respect to the two orifices 21 and 27. The circular collar 29 provides a cup-shaped hollow space 28 downstream of the face of the orifice member 25 which accordingly forms the bottom of this hollow space 28 and which is provided with a concave cavity 31 that may be provided in support of the action of a rounded blowing off edge 30 of the circular collar 29 at the axial end of the hollow space 28 the axial length of which corresponds to about 1.5 to 2.5 times the inner diameter of the circular collar.

With the additional arrangement of such a circular collar 29 coaxial with the two orifices 21 and 27 for forming the cup-shaped hollow space 28 downstream of the same the advantage will be obtained that the water stream ejecting from the orifice 27 creates a vortex motion around the axis of the hollow space 28 with the abrasive laden air stream as ejected from the orifice 21 being located in the center of this vortex motion. This specific vortex motion produces in co-operation with the tooth surface against which the ejecting air and water streams are directed a venturi-like effect which may be influenced by the spacing of the rounded blowing off edge 30 from the tooth surface so that the relatively higher velocity of the abrasive laden air stream within the core of the vortex motion is balanced with the exit speed of the spray mist at the circular gap between the blowing off edge 30 of the circular collar 29 and the tooth surface. The abrasive laden air stream ejecting from the orifice 21 and being surrounded by the water stream ejecting from the nozzle 27 is therefore more uniformly pressed against the tooth surface so that at the end of the prophylactic procedure a less eroded tooth surface as before experienced will be left with a characteristic appearance of the tooth surface that depending of course on the skill of the dentist no longer will need any subsequent polishing treatment of the tooth surface. This accordingly enamel protecting cleaning effect of the hollow space 28 as provided downstream of the two orifices 21 and 27 of the nozzle head as provided by the circular collar 29 depends of course also from other parameters such as especially the kinetic energy of the air and water streams and the kind of abrasive material which is used for the mixture with the air stream and further of the dimensions of the hollow space 28 in relation to the dimensions of the orifices 21 and 27 so that with the realization of such a hollow space with the provision of a similar circular collar the inner wall of which may be covered with a lubricant being resistent to the abrasive material and to water for also different designs of such a nozzle head such parameters have to find a prior apparatus specific consideration by the evaluation of experimental data which may necessitate various minor modifications by those skilled in the art.

It accordingly should be understood that various modifications and variations will no doubt occur to those skilled in the various arts to which this invention pertains. All such modifications and variations which basically rely on the teachings through which this disclosure has advanced the art are therefore properly considered within the scope of this invention as defined by the appended claims.

What is claimed is:

1. A nozzle head for the hand piece of a prophylactic apparatus for cleaning teeth, comprising a connector having two axially contiguous interconected members, an inner tube, ending in a first orifice, as a supply conduit for an abrasive powder material in mixture with air under pressure, and an outer tube, ending in a second orifice, as a supply conduit for water under pressure, the outer tube being fixed to the one member of the connector as arranged coaxial to the inner tube with a circular gap inbetween, over a portion of the length of the inner tube extending to said first orifice of the outer tube, said connector having two axially parallel bores adapted for an interconnection of first and second supply lines with said inner and outer tubes, said two bores of the connector being interconnected through a transverse bore extending at a right angle to their axes; the improvement comprising:

said two members of said connector being positioned with respect to each other with an axis that is in common with the one bore of said two bores through which said first supply line is connected in said one member of the connector to said inner tube.

the other bore of said two bores through said second supply line is connected to said outer tube being provided in the other member of said connector, said transverse bore extending between the two members of said connector, said one bore being provided in a centering pin of said one member of the connector, said other member of the connector being fixed on this centering pin and being provided with an outer thread for a screw connection with the hand piece.

2. A nozzle head according to claim 1, wherein said one member of the connector is provided with an axial through bore which at its one end is provided with a first enlarged centering bore into which said outer tube is fixedly inserted and which at its other end is provided with a second centering bore into which a hollow plug is fixedly inserted, this hollow plug centering a fixation end of the inner tube opposite its orifice and serving as a slip-on means for said first supply line.

3. A nozzle head according to claim 2, wherein a partial length of said axial through bore intermediate its two centering bores for said outer tube and said hollow plug, respectively, is provided with a diameter portion allowing an airtight insertion of the fixation end of the inner tube.

4. A nozzle head according to claim 2, wherein a hollow plug is fixedly inserted into the axially parallel bore of the second member of said connector, the two hollow plugs being provided with differently axially projecting lengths.

5. A nozzle head according to claim 1, wherein the orifice of the inner tube is centered by means of a screw-in orifice member of the outer tube which provides said second orifice with a cross-sectional area equal to or less than the cross-sectional area of said circular gap.

6. A nozzle head according to claim 1 wherein a portion of the length of the inner tube over which the outer tube is arranged coaxial to the inner tube extends along a continuous curvature such as to afford accessibility to the teeth and improved visibility of the work area.

7. A nozzle head according to claim 6 wherein the curvature is such that the central angle between the common axis of the two members of the connector and the common axis of the two orifices is about 107.5° + or −2.5°.

8. A nozzle head according to claim 6 wherein a circular collar is provided in a coaxial arrangement with said two orifices and projects downstream therefrom forming a cup-shaped hollow space downstream of said orifices in which the surrounding ejected water generates a vortex motion around the axis of said hollow space when the collar is brought into close proximity with the teeth, said air mixture being projected into said area of vortex motion.

9. A nozzle head for the hand piece of a prophylactic apparatus for cleaning teeth, comprising a first orifice for a central ejection of air under pressure in mixture with an abrasive powder material and a second coaxial orifice for a surrounding ejection of water under pressure from an annular passageway coaxial with and surrounding said central passageway; the improvement comprising:

a circular collar in a coaxial arrangement with said two orifices and projecting downstream therefrom forming a cup-shaped hollow space downstream of said orifices in which the surrounding ejection of water generates a vortex motion around the axis of said hollow space when the collar is brought into close proximity with the teeth, said air mixture being projected into said area of vortex motion, the axial length of this hollow space being larger than the inner diameter of said second orifice.

10. A nozzle head according to claim 9, wherein said circular collar is axially adjustable with respect to said two orifices for varying the axial length of said hollow space.

11. A nozzle head according to claim 10, wherein said circular collar is axially adjustable by means of a fine-pitch thread.

12. A nozzle head according to claim 9, wherein said hollow space is provided with an axial length corresponding to about 1,5 to 2,5 times the inner diameter of the circular collar.

13. A nozzle head according to claim 9, wherein the bottom of said hollow space is provided with an annular concave cavity.

14. A nozzle head according to claim 9, wherein said circular collar is provided with a rounded blowing-off edge.

15. A nozzle head according to claim 9, wherein the inner wall of said circular collar is covered with a lubricant being resistent to the abrasive powder material and to water.

* * * * *